United States Patent [19]

Slaugh et al.

[11] 4,417,000

[45] Nov. 22, 1983

[54] DIMETHYL ETHER PROCESS

[75] Inventors: Lynn H. Slaugh, Cypress; Robert C. Ryan, Houston, both of Tex.

[73] Assignee: Shell Oil Company, Houston, Tex.

[21] Appl. No.: 405,112

[22] Filed: Aug. 4, 1982

[51] Int. Cl.$^3$ .................. C07C 27/06; C07C 41/01
[52] U.S. Cl. .................................. 518/713; 518/714
[58] Field of Search ............................. 518/713, 714

[56] References Cited

U.S. PATENT DOCUMENTS

| | | | |
|---|---|---|---|
| 4,098,809 | 7/1978 | Pagani | 518/714 |
| 4,107,089 | 8/1978 | Bondar | 518/714 |
| 4,375,424 | 3/1983 | Slaugh | 518/713 |

*Primary Examiner*—Howard T. Mars
*Attorney, Agent, or Firm*—Ronald L. Clendenen; Ronald R. Reper

[57] ABSTRACT

Dimethyl ether is produced from syngas in high yield utilizing a physical mixture of two catalyst components: a first component comprising copper-zinc and alkali metal supported on alumina, and a second component comprising tungsten oxide supported on silica-alumina.

5 Claims, No Drawings

DIMETHYL ETHER PROCESS

FIELD OF THE INVENTION

This invention relates to a process for the conversion of syngas to dimethyl ether.

BACKGROUND OF THE INVENTION

There are many catalysts that are known for the conversion of syngas to methanol. However, thermodynamic considerations limit the syngas conversion per pass to the 20-30% range for methanol production. Thus, substantial amounts of costly syngas recycled are required to produce methanol. On the other hand, such thermodynamic limits do not exist when converting syngas to dimethyl ehter, and, hence, very deep conversions are possible when preparing dimethyl ether. Dimethyl ether is a very useful chemical intermediate for the conversion to other useful products. In principle then, dimethyl ether could be a more attractive intermediate from a cost input than is methanol for the production of other products.

U.S. Pat. No. 4,098,809, issued July 4, 1978, generally discloses the use of a copper/zinc/chromium catalyst combined with alumina for the conversion of a mixture of CO, $CO_2$ and $H_2$, wherein the quantity of CO is in excess of the stoichiometric value, to dimethyl ether.

Application Ser. No. 313,420, filed Oct. 21, 1981, discloses the use of a copper/zinc catalyst supported on alumina having a sodium concentration of less than 700 ppm is useful for converting syngas to dimethyl ether in high yield. It is also known that the use of certain alkali metal oxidic compounds such as, for example, potassium carbonate or potassium oxide, as promotors of catalysts utilized in hydrocarbon processes, extends the life of these catalysts. The addition of alkali metals, however, to catalysts such as a copper-zinc-chromium/alumina catalyst of U.S. Pat. No. 4,098,809 or the copper-zinc/alumina catalysts of Ser. No. 313,420, kills the selectivity of these catalysts to dimethyl ether and causes them to produce primarily methanol. It has been found that alkali metal dopants can be utilized for a copper-zinc alumina catalyst, while at the same time maintaining selectivity to the dimethyl ether, by utilizing a physical mixture of two catalyst components; a first component comprising said alkali metal doped copper-zinc/alumina catalysts, and a second component comprising $WO_3$/silica-alumina component. It has been noted that the addition of $WO_3$ to silica-aluminas used as catalysts in hydrocarbon processes provides for longer life thereof.

SUMMARY OF THE INVENTION

This invention relates to a process for converting syngas into dimethyl ether with substantial yields. Particularly, it relates to a catalyst combination and process wherein the carbon monoxide which is converted to hydrocarbons is converted with a high selectivity to dimethyl ether of greater than about 85, preferably greater than about 90 mol percent. The catalyst utilized comprises a physical mixture of two components; a first component comprising an alkali metal oxidic compound promoted copper-zinc catalyst supported on an alumina carrier and a second component comprising tungsten oxide ($WO_3$) supported on a silica-alumina, alumina or silica carrier. Said first component comprises from about 25 to about 75 percent by volume of the total catalyst volume. The use of the two-component catalyst system provides a catalyst having a high selectivity to dimethyl ether, a long life, and a low selectivity to methane formation. The catalyst mixture is readily regenerated.

DESCRIPTION OF THE PREFERRED EMBODIMENTS

The catalyst utilized in the instant process comprises a physical mixture of two catalyst components; the first component comprising alkali metal-copper-zinc-/alumina, and a second component comprising tungsten oxide/silica-alumina.

The first component comprises a copper-zinc catalyst supported on a porous alumina support and doped with a suitable alkali metal oxidic compound. This component will contain copper (measured as the metal) ranging from about 2% to about 15% by weight, basis total catalyst, more preferably, ranging from about 3% by weight to about 7% by weight. The zinc (measured as the metal) will range from about 2% by weight to about 8% by weight of the total catalyst, preferably, from about 3% by weight to about 7% by weight. The amount of alkali metal dopent present, measured as a metal, will range from about 0.1 to about 1, preferably from about 0.15 to about 0.6, and more preferably from about 0.2 to about 0.4 gram equivalent weights per kilogram (gew/kg). As used herein, alkali metal shall mean lithium, sodium, potassium, rubidium and cesium.

The support that is utilized to prepare the first component is an alumina support, preferably a gamma alumina support. The support surface area is generally greater than about 100 $m^2/g$, and preferably will range from about 150 to about 500 $m^2/g$.

The alumina employed can be any of the variety of available aluminas or alumina hydrates, such as alumina gel, activated alumina, gamma alumina, etc. Regarding purity of the alumina, it may be stated that small amounts of impurities are not generally detrimental. The most suitable aluminas for use in the present invention are found to be those having a high surface area, for instance, alumina having a surface area of at least about 100 $m^2/g$. The alumina may contain minor amounts of other compounds such as silica. Aluminas are readily available commercially which are readily usable in the instant invention. The following table lists several commercial aluminas and their properties which are found suitable.

| Alumina | Surface Area, $m^2$g | Pore Vol. Co/gm | Na, ppm | $SO_4^=$, % wt | $Fe_2O_3$, % wt | $Cl,^-$ % wt |
|---|---|---|---|---|---|---|
| CCI[a] | 252 | 0.8 | 160 | 0.06 | — | 0.02 |
| KA-201[b] | 365 | 0.42 | 600 | 0.03 | — | 0.01 |
| RA-1[c] | 263 | 0.26 | 4700 | 0.02 | 0.18 | — |
| ACCO[d] | 225 | 0.68 | 580 | 0.6 | — | 0.6 |
| Norton | 218 | 0.62 | 0.51 | 0.03 | — | 0.03 |
| CATAPAL[e] | 348 | 0.91 | | | | |
| FILTROL[f] | 214 | 0.82 | | | | |

[a]Catalysts & Chemicals, Inc., now United Catalysts
[b]Kaiser
[c]Reynolds Corp.
[d]American Cyanamid Corp.
[e]Conoco Corp.
[f]Filtrol Corp.

The first catalyst component can be prepared in a number of acceptable fashions. One typical method of preparation of this first component catalyst is to impregnate the alumina support with solubilized salts of copper and zinc and alkali metal. The salts must be soluble in a suitable solubilizing media, either organic or inorganic. Water is a preferred solubilizing media. Suitable salts for copper and zinc are, for example, chlorides, bromides, nitrates, acetates, lactates and the like. Nitrates are a preferred salt. Suitable salts of the alkali metal are the inorganic alkali metal oxidic compounds such as hydroxides, carbonates and oxides or compounds which upon calcination decompose to the alkali metal oxidic compounds, such as for example, nitrates bicarbonates, carboxylates such as acetates, oxylates and lactates. A preferred alkali metal impregnating compound is alkali metal hydroxide. The impregnation of the support may be carried out in one step utilizing both metals dissolved in a solution, or it may be carried out in a multi-step process, using each of the metal salts dissolved in individual impregnating solutions, with the impregnation taking place sequentially. The impregnating step(s) may be repeated one or more times to provide the optimum metal loading. A preferred impregnating process is the so-called "dry impregnation technique" wherein just a sufficient amount of impregnating solution is used such that all the pore volume in the carrier is filled and no excess solution is left after impregnation. The next step is to dry and calcine the impregnated material. The drying and calcining can be carried out in individual steps. For example, drying can be carried out at temperatures up to about 150° C. followed by the calcining step at temperatures ranging from about 400° C. to about 900° C. Preferably, the drying and calcining are carried out in one continuous step heating the material slowly through the low temperature ranges to dry the material and then raising the temperature to the calcining conditions. The purpose of the calcining is to convert the soluble metal salts into what is believed to be oxides upon the support material. Calcining is carried out in a neutral or oxidizing atmosphere, air being the preferred atmosphere. Nitrogen is also a suitable alternative atmosphere. Catalysts that are calcined at too low of a temperature, i.e. below about 400° C., do not provide for sufficiently active catalysts. Catalysts which calcined at too high of a temperature, i.e. above about 900° C., will have a reduced surface area and also a reduced activity. The drying times are not critical and depend upon temperatures. These times are readily determined by simple experimentation. Five minutes to 10 hours are usually sufficient, although longer times are acceptable.

To provide for an active and selective catalyst the calcined material must be reduced by heating in a suitable reducing atmosphere. While not wishing to limit this invention, it is believed that the reduction process must at least partially reduce the copper from the +2 oxidation state to the lower oxidation states but most not be so severe as to reduce the zinc from the +2 state to the lower oxidation state. The alkali metal oxide should not be affected by the reducing conditions. Reducing conditions range from about 100° C. to about 275° C. Suitable reducing atmospheres are, for example, hydrogen atmospheres and carbon monoxide atmospheres. Hydrogen is the preferred reducing medium.

In an optional preparative technique the alkali metal compound is added to the alumina support at a time in the preparation different from that of the addition of the copper and zinc. For example, the alumina support may be first impregnated with a suitable copper and a suitable zinc compound, dried and calcined, and then reimpregnated with a suitable alkali metal compound, followed by redrying, optional recalcination, and reduction. Alternatively, the alumina support can be impregnated with suitable copper and zinc salts, dried, calcined, reduced, and then reimpregnated with a solution containing suitable alkali metal salts and subsequently redried.

A second catalytic component utilized in the instant process comprises tungstic oxide supported on a support selected from silica-alumina, alumina and silica. It has been found that the highest selectivity to dimethyl ether is obtained using silica-alumina as the support, the next highest selectivity is obtained using alumina, and the lowest selectivity is obained using silica. The silica-alumina is thus the preferred support. This catalyst component is prepared by impregnating a suitable support with a solution of a tungsten salt, this salt being decomposable upon calcining to a tungsten oxide.

The porous silica supports that are preferably used in the preparation of the instant catalysts are readily available commercially and are known as silica gels which are essentially substantially dehydrated amorphous silica. These materials are available in various density grades, from low density with surface area ranging from about 100–200 m$^2$/g, to regular density with surface areas up to about 800 m$^2$/g. These commercially available materials are used as desiccants, selective adsorbents, catalysts and catalyst supports. The porous silica may contain minor proportions of other materials without departing from the scope of the invention such as for example, alumina and carbon. Examples of commercially available silica gels and their properties are shown in the table below.

| Support | Surface Area, m$^2$/g | Pure Vol, cc/g | Density g/cc | Particle Size |
|---|---|---|---|---|
| Davison* Grade 952 SiO$_2$ | 300 | 1.65 | 0.35 | 70 mesh (avg) |
| Davison Grade 57 SiO$_2$ | 300 | 1.0 | 0.4 | <100 mesh |
| Davison Grade 03 SiO$_2$ | 750 | 0.43 | 0.7 | 8 mesh (avg) |

*Manufactured by Davison Chemical Div., W. R. Grace & Co.

The aluminas used to prepare the second component are the same as those used to prepare the first component and are described above.

The preferred supports used to prepare the catalysts of this invention are the silica-aluminas which are commercially available and generally employed as cracking catalysts. Preferred silica-alumina catalyst supports contain from about 70 to 90% by weight of silica. A particularly valuable commercially available silica catalyst support is the Davison Grade 980-25 (manufactured by Davison Chemical Division, W. R. Grace & Co.). The silica-alumina support can also be prepared in a conventional fashion, as for example by co-precipitation, co-gellation, or by spray drying.

The first step in the preparation of the catalyst is to impregnate the carrier with a tungsten salt which would decompose to the oxide upon heating. The salt(s) must be soluble in a suitable solubilizing media, either organic or inorganic. A preferred impregnating solution comprises an aqueous solution of ammonium metatungstate. The impregnation of the support may be carried out in one step utilizing the impregnating solution, or it may be carried out in a multi-step process, sequentially impregnating the material, drying, calcining, reimpregnating, drying, calcining, etc. A preferred impregnating process is the so-called "dry impregnation" when just a sufficient amount of impregnating solution is used such that all the pore volume in the carrier is filled and no excess solution is left after impregnation. After impregnation, the next step is to dry and calcine the impregnated material. The drying and calcining can be carried out in individual steps. For example, drying can be carried out at a temperature ranging up to about 150° C. followed by calcining step at temperatures ranging from about 600° C. to about 800° C. Preferably, the drying and calcining are carried out in one continuous step, heating the material slowly through the low temperature ranges to dry the material and then raising the temperature to the calcining conditions. The purpose of the calcining is to convert the soluble tungsten salt to an oxide upon the support material. Calcining is carried out in an oxidizing atmosphere, air being a preferred atmosphere. Nitrogen is not a suitable alternative atmosphere. The drying step is preferably carried out in the initial stages of calcining step. Drying and calcining times are not critical and depend on temperatures. These are readily determined by simple experimentations. Five minutes to ten hours are usually sufficient, although longer times are acceptable.

The concentration of $WO_3$ will range from about 0.5 to about 25 preferably from about 1 to about 10 percent by weight of the second component (measured as tungsten metal) basis total catalyst. After calcining, this catalyst component is typically activated in a neutral or reducing atmosphere at a temperature ranging from about 200° C. to about 400° C.

The catalyst used in the instant process comprises a physical mixture of two catalytic components. This mixture can take place in various forms. For example, the two components can be intimately mixed and then inserted in the reactor. Alternatively, alternate layers of the two catalytic components can be utilized in the reactor. Variations of the above two schemes will be apparent to one having skill in the art. The first catalytic component will comprise from about 25% to about 75% by volume of the catalysts utilized.

The catalysts of the instant invention are used in typical fashion, for example, in packed beds or in fluidized beds. In a typical operation, a process stream containing hydrogen and carbon monoxide is passed over the catalyst bed at a temperature ranging from about 250° C. to about 325° C. and at a pressure ranging from about 40 to about 300 atmospheres. The ratios between the reagents are not particularly critical with molar ratios of $CO/H_2$ between about 1:10 and about 3:1 being preferable. The gaseous hourly space velocity can be varied, preferentially, between about 1,000 hours$^{-1}$ and about 10,000 hours$^{-1}$, but also with higher spacial velocities satisfactory results can be obtained. The reaction mixture can also contain gases which are inert to the reaction concerned, such as, for example, nitrogen. Carbon dioxide may also be present.

Preparation of the catalysts used in the instant invention and the utilization of these catalysts in the instant process will be further described below by the following illustrative embodiments which are provided for illustration and are not to be construed as limiting the invention.

ILLUSTRATIVE EMBODIMENTS

Catalyst Preparation

The following example describes a typical preparation of the catalysts used in the instant process.

Preparation of Copper-Zinc-Sodium on Alumina 7.2 Grams (24.4 m moles) copper nitrate and 7.8 g zinc nitrate (26.2 m moles) were dissolved in water to 28 ml volume. This solution was added to 30 g of 20–30 mesh (U.S. standard testing sieve) Norton $Al_2O_3$ (218 m$^2$/g surface area) and kneaded. After 30 minutes the particles were loaded in a 1" vycor tube, a flow of dry air at 500 ml/min downstream was set, and the temperature programmed to 500° C. in 2 hours. The catalyst was cooled and then impregnated with a water solution of the appropriate amount of sodium hydroxide. After 30 minutes, the catalyst was again loaded in the vycor tube, a 500 ml/min. nitrogen flow set, and the temperature was programmed to 300° C. in 1 hour.

Preparation of Tungsten on Silica-Alumina 2.6 Grams ammonium metatungstate dissolved in 20 ml water was added to 30 g of 20–30 mesh Davison 980-25 silica-alumina. After 30 minutes, the particles were loaded in a 1" vycor tube, a downflow of 500 ml/min. nitrogen set, and the temperature programmed to 700° C. in 3 hours.

Process

A series of catalysts both according to this invention are prepared as described above. The basic catalyst comprises a first component of 5% Cu and 5% Zn on a Norton gamma alumina carrier (surface area about 218 m$^2$/g and a second component comprises 6%w W on a Davison 980-25 silica-alumina carrier. Sodium concentrations on the first component are varied as indicated in Table I.

A mixture of the copper-zinc sodium on alumina and the tungsten on silica-alumina were loaded in the Center section of 1"0 ss reactor tube. Hydrogen at 800 ml/min. at 1 atmosphere was passed downstream and the temperature programmed to 270° C. in 2 hours. After cooling to ambient temperature, the syngas at a molar ratio of 1:1 was added at the appropriate pressure and space velocity, followed by increase in temperature to the desired reaction temperatures. Results are shown in Table I below. Results obtained by substituting different bases for the sodium in the $Cu/Zn/Na/Al_2O_3$ catalyst are shown in Table II below.

TABLE I

DIETHYL ETHER FROM SYNGAS: PHYSICAL MIXTURE CATALYSTS
PRESSURE = 900 PSIG, GHSV = 3000
CO:H$_2$ = 1:1
CATALYST:(a) 5% Cu/5% Zn/Alkali Metal/Norton Al$_2$O$_3$ + WO$_3$/SiO$_2$.Al$_2$O$_3$

| Example | Alkali Metal Added % Wt | (b) (gew/kg) | RXN Temp. °C. | CO Conv. % | MOLAR SELECTIVITY, % | | | |
|---|---|---|---|---|---|---|---|---|
| | | | | | CH$_4$ | C$_2$–C$_7$ | Me$_2$O | CH$_3$OH |
| 1 | 0.1 Na | (0.043) | 296–299 | 40.3 | 1.5 | 4.0 | 93.2 | 1.4 |

TABLE I-continued

DIETHYL ETHER FROM SYNGAS: PHYSICAL MIXTURE CATALYSTS
PRESSURE = 900 PSIG, GHSV = 3000
CO:H$_2$ = 1:1
CATALYST:[a] 5% Cu/5% Zn/Alkali Metal/Norton Al$_2$O$_3$ + WO$_3$/SiO$_2$.Al$_2$O$_3$

| Example | Alkali Metal Added % Wt | [b] (gew/kg) | RXN Temp. °C. | CO Conv. % | MOLAR SELECTIVITY, % | | | |
|---|---|---|---|---|---|---|---|---|
| | | | | | CH$_4$ | C$_2$-C$_7$ | Me$_2$O | CH$_3$OH |
| 2 | 0.2 Na | (0.087) | 292–296 | 40.6 | 1.0 | 3.6 | 94.3 | 1.1 |
| 3 | 0.5 Na | (0.22) | 289–299 | 38.9 | 0.1 | 0.4 | 98.6 | 0.9 |
| 4 | 1.0 Na | (0.43) | 290–301 | 42.1 | 0.3 | 0.4 | 98.5 | 0.8 |
| 5 | 1.0 Na | (0.43) | 285–293 | 51.5 | 0.6 | 0.3 | 98.2 | 1.0 |
| 6 | 1.5 Na | (0.65) | 289–295 | 26.7 | 0 | 0.8 | 98.4 | 0.8 |
| 7 | 2.0 Na | (0.87) | 291–297 | 30.7 | 0.2 | 1.2 | 98.0 | 0.6 |

[a]1:1 Volume mixture of 5% Cu/5% Zn/Norton Al$_2$O$_3$ and WO$_3$/SiO$_2$.Al$_2$O$_3$ (6% w) (6% wt W; 980-25 Davison SiO$_2$.Al$_2$O$_3$).
[b]gew = gram equivalent weight The above experiments were repeated but using lithium potassium or cesium as the promoter for the first component rather than sodium. The results are shown in Table II. Comparative experiments A, B and C using calcium demonstrates that alkaline earth metals are not as effective as alkali metals or promoters.

The above experiments were repeated but using alumina and silica as supports for the tungsten catalyst. The results are shown in Table III.

TABLE II

DIETHYL ETHER FROM SYNGAS: PHYSICAL MIXTURE CATALYSTS
PRESSURE = 900 PSIG, GHSV = 3000
CO:H$_2$ = 1:1
CATALYST:[a] 5% Cu/5% Zn/Alkali Metal/Norton Al$_2$O$_3$ + WO$_3$/SiO$_2$.Al$_2$O$_3$

| Example | Alkali Metal Added % Wt | [b] (gew/kg) | RXN Temp. °C. | CO Conv. % | MOLAR SELECTIVITY, % | | | |
|---|---|---|---|---|---|---|---|---|
| | | | | | CH$_4$ | C$_2$-C$_7$ | Me$_2$O | CH$_3$OH |
| 8 | 0.25 Li | (0.36) | 296 | 44.6 | 0.7 | 4.2 | 92.6 | 2.4 |
| 9 | 0.5% Li | (0.72) | ~292 | 25.4 | 0.9 | 1.1 | 96.6 | 1.4 |
| 10 | 1.0% Li | (1.45) | ~292 | 21.5 | 1.0 | 0.8 | 97.2 | 1.0 |
| 11 | 1% K | (0.26) | 298–301 | 49.1 | 0.6 | 0.6 | 98.4 | 0.5 |
| 12 | 1.5% K | (0.38) | 298–300 | 43.6 | 0.6 | 0.9 | 98.4 | 0.2 |
| 13 | 2% K | (0.51) | 290–295 | 34.3 | 0.9 | 1.0 | 97.0 | 1.1 |
| 14 | 4% K | (1.02) | 291–292 | 20.6 | 1.2 | 2.1 | 96.3 | 0.4 |
| 15 | 4% Cs | (0.30) | ~297 | 42.5 | 0.9 | 1.9 | 96.7 | 0.5 |
| A | 1% Ca | | 288–293 | 33.3 | 0.9 | 4.4 | 68.6 | 26.2 |
| B | 1% Ca | | ~304 | 38.6 | 0.9 | 0.4 | 89.8 | 8.9 |
| C | 4% Ca | | ~292 | 20.2 | 0.4 | 4.6 | 86.1 | 9.1 |

[a]1:1 Volume mixture of 5% Cu/5% Zn/Norton Al$_2$O$_3$ and WO$_3$/SiO$_2$.Al$_2$O$_3$ (6% w) (6% wt W; 980-25 Davison SiO$_2$.Al$_2$O$_3$).
[b]gew = gram equivalent weight

TABLE III

DIETHYL ETHER FROM SYNGAS:
PHYSICAL MIXTURE CATALYSTS
PRESSURE = 900 PSIG, GHSV = 3000
CO:H$_2$ = 1:1
CATALYST:[a] 5% Cu/5% Zn/1% w Na/Norton Al$_2$O$_3$ + WO$_3$/Support

| Example | [b] (gew/kg) | RXN Temp. °C. | CO Conv. % | MOLAR SELECTIVITY, % | | |
|---|---|---|---|---|---|---|
| | | | | CH$_4$ | Me$_2$O | CH$_3$OH |
| 15[a] | (0.87) | 288 | 22.6 | | 87.9 | 8.5 |
| 16[b] | (0.87) | 287–293 | 46.2 | 0.4 | 96.4 | 3.2 |

[a]1:1 Volume mixture of 5% w Cu/5% w Zn/1% w Na/Norton Al$_2$O$_3$ and WO$_3$/SiO$_2$ (6% wt W; Davison Grade 57 SiO$_2$).
[b]1:1 Volume mixture of 5% w Cu/5% w Zn/1% w Na/Norton Al$_2$O$_3$ and WO$_3$/Al$_2$O$_3$ (6% wt W; RA-1 Al$_2$O$_3$).
[c]gew = gram equivalent weight.

We claim:

1. A process for the production of dimethyl ether in high yield from carbon monoxide and hydrogen which comprises contacting said carbon monoxide and hydrogen at a temperature between about 250° C. and about 350° C. and a pressure between about 30 to about 300 atmospheres with a catalyst comprising a physical mixture of two components; a first component comprising an alkali metal oxide promoted copper-zinc catalyst supported on an alumina carrier and a second component comprising tungsten oxide supported on a carrier selected from silica-alumina, silica or alumina wherein said first component comprises from about 25 to about 75 percent by volume of the total catalyst volume.

2. The process of claim 1 where in the first component the copper ranges from about 2% to about 15% by weight of said first component, the zinc ranges from about 2% to about 8% by weight of the first component and the alkali metal ranges from about 0.1 to about 1 gew/kg of said first component and where in the second component the tungsten ranges from about 0.5 to about 25% by weight, basis tungsten metal, of said second component.

3. The process of claim 2 wherein the copper ranges from about 3% to about 7%, the zinc ranges from about 3% to about 7%, the alkali metal ranges from about 0.15 to about 0.6 gew/kg and the tungsten ranges from 1% to about 10%.

4. The process of claim 3 wherein the alkali metal ranges from about 0.2 to about 0.4 gew/kg.

5. The process of claims 1, 2, 3, or 4 wherein the first component is supported on a gamma alumina carrier and the second component is supported on a silica-alumina carrier.

* * * * *